United States Patent [19]

Moody

[11] Patent Number: 5,721,211

[45] Date of Patent: *Feb. 24, 1998

[54] COMPOSITIONS AND METHODS FOR TREATING SMALL CELL AND NONSMALL CELL LUNG CANCERS

[75] Inventor: Terry W. Moody, Germantown, Md.

[73] Assignee: The George Washington University, Washington, D.C.

[*] Notice: The term of this patent shall not extend beyond the expiration date of Pat. No. 5,273,963.

[21] Appl. No.: 171,701

[22] Filed: Dec. 22, 1993

Related U.S. Application Data

[63] Continuation-in-part of Ser. No. 676,987, Mar. 29, 1991, Pat. No. 5,273,963.

[51] Int. Cl.$^6$ .................................................. A61K 38/22
[52] U.S. Cl. ............................ 514/12; 514/21; 530/324; 530/327; 530/399
[58] Field of Search ....................... 514/12, 21; 530/324, 530/327, 399

[56] References Cited

U.S. PATENT DOCUMENTS

| | | | |
|---|---|---|---|
| 4,079,127 | 3/1978 | Goldstein et al. | 424/177 |
| 4,082,737 | 4/1978 | McGregor et al. | 530/399 |
| 4,560,676 | 12/1985 | Merrifield | 514/12 |
| 4,612,365 | 9/1986 | Birr et al. | 530/301 |
| 4,910,296 | 3/1990 | Birr et al. | 530/324 |
| 5,217,953 | 6/1993 | Gozes et al. | 514/12 |
| 5,512,656 | 4/1996 | Wang | 530/324 |

FOREIGN PATENT DOCUMENTS 3100974  1/1982  Germany.

OTHER PUBLICATIONS

J.R. Calvo et al., "Interaction of Thymic Peptide . . . with PH1 Secretin", *Gen. Pharmac*, vol. 20, No. 4, issued 1989, pp. 503–505.

J.R. Calvo et al., "Interactions of Thymic Peptide . . . (VIP) Receptors", *Bioscience Reports*, vol. 6, No. 8, issued 1986, pp. 727–733.

Shaffer et al., "High Affinity Binding . . . Cancer Cell Lines," *Peptides*, vol. 8, issued 1987, pp. 1101–1106 see p. 1105.

J. Pichon et al., "Anti–cell Surface Monoclonal . . . (H 29 Cells)", *The EMBO Journal*, vol. 2, No. 7, issed 1983, pp. 1017–1022.

Cohen, M.H., et al., "Thymosin Fraction V and Intensive Combination . . . ", *Journal of the American Medical Association*, 241:1813–15 (1979).

Schulof, R.S., et al., "A Randomized Trial . . . ", *Journal of Biological Response Modifiers*, 4:147–58 (1985).

Chemical Abstacts, vol. 115, No. 19, Nov. 11, 1991, Abstract No. 205598r, E. Garaci et al., p. 811.

Chemical Abstracts, vol. 114, No. 7, Feb. 18, 1991, Abstract No. 56079x, M. Lee et al., p. 103.

Moody et al., *Cancer Res.*, vol. 53, pp. 5214–5218, 1993.

*Primary Examiner*—Chhaya D. Sayala
*Attorney, Agent, or Firm*—Rothwell, Figg, Ernst & Kurz

[57] ABSTRACT

Compositions and methods of use thereof for treating small cell and nonsmall cell lung cancers in mammals are disclosed. The compositions comprise substances that inhibit the lung cancer cell growth and proliferation actions of the biological response modifier vasoactive intestinal polypeptide, such as specific thymosins or analogues, derivatives and fragments thereof, anti-vasoactive intestinal polypeptide receptor polyclonal or monoclonal antibodies, and antibodies directed against the vasoactive intestinal polypeptide molecule itself.

4 Claims, 6 Drawing Sheets

FIG. 3A
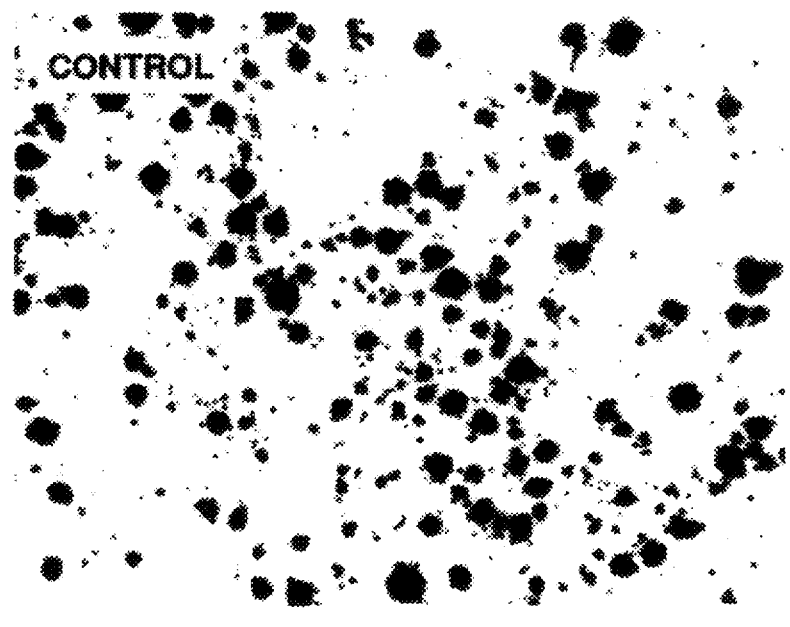
FIG. 3B

COMPOSITIONS AND METHODS FOR TREATING SMALL CELL AND NONSMALL CELL LUNG CANCERS

CROSS-REFERENCE TO RELATED APPLICATIONS

This application is a continuation-in-part of U.S. application Ser. No. 07/676,987, filed Mar. 29, 1991, now U.S. Pat. No. 5,273,963, issue date Dec. 28, 1993.

BACKGROUND OF THE INVENTION

1. Field of the Invention

The invention relates generally to the treatment of lung cancer. More particularly, it relates to certain biological response modifiers and their use in treating neuroendocrine small cell lung cancers and non-neuroendocrine nonsmall cell lung cancers.

2. Description of the Related Art

Lung cancer is a serious public health problem that kills approximately 150,000 people in the United States annually. Minna, J. D., et al. in *Cancer, Principles and Practice of Oncology*, eds., DeVita, V. T., Jr., et al., Lippincott, Philadelphia (1985), pp. 507-599.

Lung cancers can be grossly divided into small cell lung cancer (SCLC) which accounts for approximately 25% of lung cancer cases and nonsmall cell lung cancer (NSCLC). NSCLC can be further subdivided into adenocarcinoma, lung cell carcinoma and squamus cell carcinoma, each of which account for about 25% of lung cancer cases.

SCLC is caused by a neuroendocrine tumor that undergoes remission generally after chemo- or radiation-therapy but that generally recurs after a few months, after which the patient is usually refractory to these therapeutic modalities. The tumor is initially localized to the lung, but undergoes metastasis to other organs such as the liver, lymph nodes, bone and/or brain. The median survival time of SCLC patients is 1 year.

NSCLC is treated by surgical resection, as well as by chemotherapeutic agents such as cyclophosphamide, methotrexate, ifosfamid and cis-platin. For NSCLC patients, only 25% survive for 5 years after diagnosis.

Clearly, there is a need for newer, more imaginative and more effective therapeutic approaches, such as an approach based upon endogenous biochemical factors that regulate the growth of lung cancer cells that is the subject matter of this invention.

Lung cancer cells make and secrete endogenous growth factors that regulate tumor proliferation. Moody, T., *Science*, 214:1246 (1981). For example, bombesin/gastrin releasing peptide (BN/GRP), members of a class of peptides referred to as "biological response modifiers" (BRM), are synthesized in SCLC cells as a high molecular weight protein that is processed to a 27-amino acid, biologically active form. Sausville, E. A., et al., *J. Biol. Chem.*, 261:2451 (1985). SCLC cells use BN/GRP as an autocrine growth factor (Cuttitta, F., et al., *Nature*, 316:823 (1985); these peptides stimulate the clonal growth of such cells. Carney, D. N., et al., *Cancer Res.*, 47:821 (1987). Thus, SCLC cells synthesize and secrete BN/GRP, and BN or GRP bind to cell surface receptors and stimulate the growth of SCLC cells. The autocrine growth cycle of BN/GRP can be blocked using either monoclonal antibodies against BN (Cuttitta et al., 1985) or a BN receptor antagonist, Psi[13, 14] (Leu[14] BN). Mahmoud, S., et al., *Life Sci.*, 44:367 (1989)).

In contrast, NSCLC cells secrete transforming growth factor α (TGFα), but not BRMs such as BN/GRP. TGFα binds to cell surface receptors for epidermal growth factor (EGF), and stimulates growth of NSCLC cells. Imanishi, L., et al., *J. Natl. Cancer Inst.*, 81:220 (1989). Also, EGF stimulates the clonal growth of established NSCLC cell lines such as adenocarcinoma cell line 5M2 (Lee, M., et al., *J. Cell Biochem.*, 1991, in press), and the growth of such NSCLC cells is inhibited by an EGF receptor monoclonal antibody. Moody, T. N., *J. Cell. Biochem.*, 43:139 (1990).

Vasoactive intestinal polypeptide ("VIP"), a 28-amino acid basic peptide BRM of Mr 3324, with the sequence shown in Sequence ID No. (1) below, is synthesized in normal lung cells, and functions as a bronchodilator. Morice, A. H., et al., *Lancet* 1:457 (1984). These actions of VIP are mediated by cell surface receptors localized to alveoli and smooth muscle cells. Robberecht, P., et al., *Regul. Peptides*, 4:241 (1982). VIP receptors have also been identified on human B-lymphocyte cell lines and cells in the peripheral circulation. O'Dorisio, S., et al., *J. Immunol.*, 15:142 (1989). It has recently been found that SCLC and NSCLC cells bind VIP with high affinity. Shaffer, M. M., et al., *Peptides*, 8:1101 (1987). These observations suggest that VIP, acting through cell surface receptors on normal and malignant lung cells, regulates the growth of such cells.

$$\text{N—His—Ser—Asp—Ala—Val—Phe—Thr—Asp—Asn—Tyr—} \atop 5 \qquad\qquad\qquad\qquad 10 \qquad (1)$$

$$\text{Thr—Arg—Leu—Arg—Lys—Gln—Met—Ala—Val—Lys—} \atop 15 \qquad\qquad\qquad 20$$

$$\text{Lys—Tyr—Leu—Asn—Ser—Ile—Leu—Asn—NH2} \atop 25 \qquad\qquad \text{(SEQ ID NO:1)}$$

"Thymosin" is the name given to a class of polypeptide "hormones", isolated from the thymus glands of mammals, that exert profound effects as potentiators of the growth and differentiation of T-lymphocytes. Smith, E. L., et al. *Principles of Biochemistry*, McGraw-Hill, New York, 1983, Chapter 19. Thymosins can thus be considered to be BRMs. Members of this class include thymosin α1 ("THNα1"), a 28-amino acid peptide of 3,108 molecular weight with the following structure shown in Sequence ID No. (2):

$$\text{Ac—Ser—Asp—Ala—Ala—Val—Asp—Thr—Ser—Ser—Glu—} \atop 5 \qquad\qquad\qquad\qquad 10 \qquad (2)$$

$$\text{Ile—Thr—Thr—Lys—Asp—Leu—Lys—Glu—Lys—Lys—Glu—} \atop 15 \qquad\qquad\qquad 20$$

$$\text{Val—Val—Glu—Glu—Ala—Glu—Asn—OH} \atop 25$$

(Goldstein, A. L., et al., U.S. Pat. No. 4,079,127), and with substantial sequence homology to VIP at amino acid positions 4, 5, 7, 20 and 28; thymosin β4 (a 43-amino acid peptide, MW 4982, U.S. Pat. No. 4,395,404); thymosin α11 (a 35-amino acid peptide, U.S. Pat. No. 4,614,731); thymosin α7 (U.S. Pat. No. 4,517,119); and, thymosin β3 (a 50-amino acid peptide, U.S. Pat. No. 4,395,404).

THNα1 is known to restore cellular immunity to patients with primary immunodeficiency (Frasca, D., et al., *Eur. J. Immun.*, 17:727 (1987)), and, in patients with NSCLC, THNα1 has been reported to accelerate the reconstitution of thymic dependent immunity. Schulof, R. S., et al., *J. Biol. Response Modifiers*, 4:147 (1985).

Clinical trials with cancer patients using thymosin Fraction V (a crude mixture of thymosins isolated from thymus glands—Goldstein, A. L., et al., *Proc. Nat'l Acad. Sci. USA*, 56:1010 (1966), which contains about 0.6% of THNα1) and THNα1 itself have yielded equivocal results with regard to the value of immunopotentiation by these polypeptides in the course of the cancers. Thymosin Fraction V in combination with intensive remission-induction chemotherapy in patients with small cell bronchogenic carcinoma reportedly significantly prolonged survival times relative to other treatment groups. Cohen, M. H., et al. *J. Am. Med. Assoc.*, 241:1813 (1979); Johnston-Early, A., et al., *J. Am. Med. Assoc.*, 244:2175 (1980). However, more recently it has been reported that thymosin Fraction V did not influence the outcome in patients with SCLC who were being treated concurrently with induction chemotherapy and radiation therapy (Scher, H. I., et al., *Cancer Res.*, 48:1663 (1988)).

In patients with NSCLC, thymosin Fraction V did not improve the results with vindesine-adriamycin-cis-platin chemotherapy. Valdivieso, M., et al., ASCO Abstracts, C-636 (1981); Bedikian, A. Y., *Am. J. Clin. Oncol.* (CCT) 7:399 (1984). THN$\alpha$1 $\alpha$1 itself also failed to influence the course of NSCLC in a small group of patients. Dillman, R. D., et al., *J. Biol. Resp. Med.*, 6:263 (1987). In contrast, in a randomized trial to evaluate the immunorestorative properties of synthetic THN$\alpha$1 in postradiation therapy patients with NSCLC, thymosin normalized T-cell function and was associated with significant improvements in relapse-free and overall survival. Schulof, R. S., et al., *J. Biol. Resp. Med.*, 4:147 (1985).

Because of these uncertainties regarding the effects of the thymosins in patients with advanced lung cancers, we have sought, and have found, a more basic and biochemical approach to the inhibition of proliferation of SCLC and NSCLC cells, an approach based on the roles of growth regulation factors operative in lung cancer cells. A new modality for treating SCLC and NSCLC is disclosed and claimed below.

SUMMARY OF THE INVENTION

It has been found that the growth and clonal proliferation of lung cancer cells in vitro and in vivo is reduced by agents that interfere with the functional activities in such lung cancer cells of the biological response modifier VIP.

It is thus an object of this invention to disclose thymosin preparations and analogues, derivatives and fragments thereof as therapeutic modalities that will inhibit the growth and proliferation of lung cancer cells.

It is also an object of this invention to disclose polyclonal and monoclonal anti-VIP receptor and anti-VIP antibody preparations that will inhibit the growth and proliferation of lung cancer cells.

It is yet another object of this invention to provide methods for screening thymosin and antibody preparations for efficacy as inhibitors of growth and clonal proliferation of lung cancer cells.

These and other objects of the invention will become clear by reference to the specification and to the appended claims.

DETAILED DESCRIPTION OF THE DRAWINGS

FIG. 3A shows colonization of NCI-H838 lung cancer cells in the absence of 10 µM THN$\alpha$1, and FIG. 3B shows colonization of NCI-H838 lung cancer cells in the presence of 10 µM THN$\alpha$1.

DETAILED DESCRIPTION OF THE INVENTION

Figure 1:
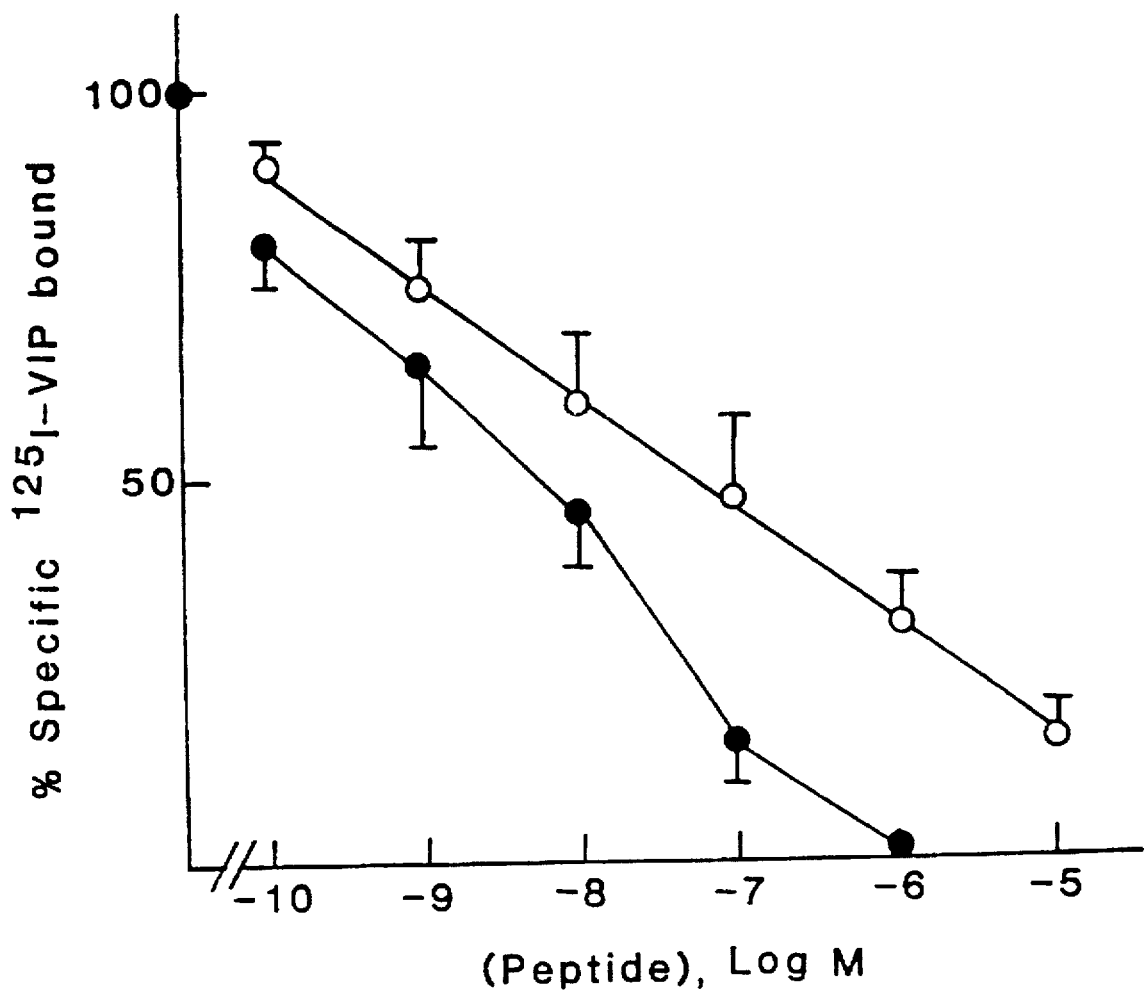
FIG. 1 is a plot of the specific binding of $^{125}$I-labeled VIP to lung cancer cell plasma membranes as a function of the log of the concentration of varying amounts of unlabeled VIP (●) and THN$\alpha$1 (○).

It has been discovered that the growth and proliferation of lung cancer cells in vitro and in vivo can be inhibited by agents that interfere with the biological, functional activities of the biological response modifier VIP in such cells. Such agents include specific thymosins, such as THN$\alpha$1 and related N-terminal and C-terminal peptides, analogues and derivatives, and anti-VIP receptor antibodies, presumably acting either to inhibit the binding of VIP to its cell surface receptors on lung cancer cells or interfere with the subsequent activities of VIP. Such agents also include anti-VIP antibodies capable of inhibiting the binding of endogenous or exogenous VIP to cell surface receptors on SCLC and NSCLC lung cancer cells and, in so doing, inhibiting the growth and proliferation of these cells. These discoveries will be reported in a future publication. Moody, T. W., et al., *Cancer Research Proceedings*, 1991, in press.

The present invention specifically is directed to inhibition of growth and proliferation of lung cancer cells by a member selected from the group consisting of thymosin $\alpha_1$ amide and thymosin $\alpha_1$-$N_{16}$(1–16) amide shown in Sequence ID No. (3).

Specific in vitro interactions of thymosins and related fragments with cell surface binding sites on lung cancer cells may be studied by standard binding assay procedures using intact lung cancer cells or plasma membranes derived therefrom. See, e.g., Blecher, M., ed., *Methods In Receptor Research, Parts I and II*, Marcel Dekker, N.Y., 1976; Posner, B., ed., *Polypeptide Hormone Receptors*, Vol. 4, Marcel Dekker, N.Y., 1985; *Journal of Receptor Research*, vols. 7 and 8 (1988), which are incorporated herein by reference to the extent that they disclose binding assay procedures.

SCLC and NSCLC established cell lines may be obtained through the National Cancer Institute, Bethesda, Md. (USA) (e.g., NCI-H157, NSCLC cells; NCI-H345, SCLC cells; NCI-H292, NSCLC squamous cell carcinoma; NCI-H838, adenocarcinoma; NCI-H417, SCLC cells; H720, lung carcinoid cells; NCI-H727, lung carcinoid cells; NCI-N592, SCLC cells; EPLC-65H, squamous cell carcinoma) or from the American Type Culture Collection, Rockville, Md. (USA).

Plasma membranes from such cells may be isolated according to Lee, M., et al., *Peptides*, 11:1205 (1990), which is incorporated herein by reference.

Generally, binding competitions are set up between a tracer concentration of labeled ligand and varying concentrations of either the unlabeled counterpart of the labeled ligand or an unlabeled peptide suspected of binding to the receptor for the ligand. For example, SCLC or NSCLC cells or plasma membranes isolated therefrom are incubated with a tracer concentration of $^{125}$I-labeled VIP and a range of concentrations of unlabeled VIP or an unlabeled thymosin or fragments thereof, or an anti-VIP receptor antibody, and the amount of specific binding of the tracer at each concentration of the unlabeled ligands determined.

It has now been found that $^{125}$I-labeled VIP binds with high affinity to SCLC and NSCLC cell lines, and that VIP markedly stimulates the adenylate cyclase activity of these cells. It has also now been found that THNα1 inhibits the binding of labeled VIP to lung cancer cells, although it does so with a potency only a twentieth that of unlabeled VIP. In addition, THNα1 inhibits the stimulatory effect of VIP on second messenger cAMP production in lung cancer cells.

Direct, i.e., noncompetitive, binding of a labeled ligand to intact cells or plasma membranes may be determined. Attempts to carry out such analyses using, for example, ($^{125}$I-Tyr)-labeled THNα1 or N-terminal or C-terminal fragments demonstrated that such molecules bind with poor affinity to lung cancer cells or plasma membranes derived therefrom. These and other experiments not detailed here indicate that the thymosins may not have specific receptors. Palaszynski, E., *Biochemical Studies on Thymosin α1*, Ph.D. Thesis, George Washington University, Washington, D.C., 1981. It is thus all the more suprising and unexpected that certain thymosins have such profound inhibitory effects on the binding of VIP to its specific receptors and on the growth promoting effects of VIP in lung cancer cells.

Although $^{125}$I is a frequently used label for peptide binding studies, other markers such as chemiluminescent compounds and fluorescent molecules may be used.

Cross-linking procedures may also be used to identify ligand-receptor interactions with SCLC or NSCLC cells or plasma membranes. Generally, the tissue is incubated with a tracer concentration of a labeled ligand, without and with varying concentrations of an unlabeled ligand, until steady state binding is attained. At that point, unbound labeled ligand is removed by washing the tissue at ice bath temperature, and the bound labeled ligand is covalently cross-linked to its receptor protein by the addition of a cross-linking reagent. Thereafter, the cells or membranes are solubilized with a detergent, and the samples analyzed by SDS-PAGE electrophoresis, followed by autoradiography to determine the molecular weight of the receptor protein to which the labeled ligand had bound. A wide variety of peptide-peptide cross-linking reagents are known, such as those available from Pierce Co., Rockford, Ill. (USA), 1989 Handbook and General Catalog, pages 283–311, which is incorporated herein by reference.

It has been found from such cross-linking studies that THNα1 inhibits the cross-linking of VIP to its receptor protein of about 82 kDa located in the plasma membrane of lung cancer cells of both SCLC and NSCLC types.

Candidate anti-lung cancer peptides and antibodies may be screened in vitro in a soft agar colonization assay such as that described by Mahmoud, S., et al., *Life Sci.*, 44:367 (1989) which is herein incorporated by reference. In general, single viable lung cancer cells are plated in soft agar. After an appropriate growth period, such as 14 days, cell colonies may be stained with an appropriate cytochemical stain, and the stained cells viewed microscopically. Cytochemical stains are well known to those skilled in the art of histology.

It has been found from such in vitro colonization experiments that THNα1 dramatically reduces colony formation of lung cancer cells in vitro under conditions in which THNβ4 and VIP have little effect.

The aforementioned binding, cross-linking and colonization experiment lead to the unexpected finding that thymosins inhibit the growth of lung cancer cells by an action mediated by cell surface receptors for a BRM active in such cells.

Candidate anti-lung cancer peptides and anti-VIP receptor antibodies may be tested in vivo in a mouse model of lung cancer. For example, when SCLC cell lines such as NCI-N592 or NCI H69, or NSCLC cell lines such as NCI-H157 or NCI-H292 are injected subcutaneously into nude mice, xenografts will form. The test peptide may then be injected adjacent to the tumor, and the tumor volume measured periodically. Control mice will not receive the test peptide or will receive a placebo peptide in the same pharmaceutically acceptable vehicle. Tumor growth in experimental and control animals are compared, and test peptides ranked according to efficacy in reducing tumor size.

It has been found that THNα1 and its C-terminal (such as amino acids 4–28 and 15–28) and N-terminal (such as amino acids 1–8, 1–14, and 1–20) fragments inhibit lung cancer growth in vivo in tumors of both SCLC and NSCLC types of lung cancer cells. No toxic side effects were observed. Taken together with the binding and in vitro experiments, the data of the invention demonstrate a novel modality for treating lung cancers of both the small cell and nonsmall cell types without radiation treatment and without the need for concurrent use of the toxic classical chemotherapeutic agents, although the use of such additional modalities is not precluded by the present invention.

Anti-EGF receptor antibodies are known to inhibit the binding of this peptide hormone to its specific cell surface receptor macromolecule. Lee, M. et al, Cancer Res. Proc., 1990. Monoclonal antibodies to a human colonic adenocarcinoma cell line VIP receptor have been prepared (Kummer, W., et al., *Histochem. J.*, 22:249 (1990)) and used for histochemical identification of cells bearing this receptor.

Polyclonal and monoclonal antibodies directed against the VIP receptors on SCLC and NSCLC cells may be used to inhibit the binding of VIP to its receptors on these cells, thereby reducing the proliferative effects of VIP. These antibodies may be prepared by raising antisera and/or monoclonal antibodies against detergent-solubilized, purified forms of the SCLC and NSCLC VIP receptor macromolecules. Monoclonal antibody-producing hybridoma cells can be produced by injecting mice, such as Balb/c mice, with purified VIP receptor antigen, fusing spleen cells of hyperimmunized mice with myeloma cells, such as NSO myeloma cells, using the polyethyleneglycol technique, selecting hybridomas using the HAT growth medium, screening hybridoma supernatant fluids for the ability to immunoprecipitate cross-linked VIP receptors as well as the ability to inhibit the binding of labeled VIP to lung cancer cells, and cloning positive hybridomas. For details of these techniques, see Cuttitta, F., et al. *Nature*, 316:823 (1985); Engleman, E., et al., eds., *Human Hybridomas and Monoclonal Antibodies*, Plenum Publishing Co., N.Y., 1985; Harrell, J. G. R., ed., *Monoclonal Hybridoma Antibodies: Techniques and Applications*, CRC Press, 1982; Larrick, J. W., et al., *BioTechniques*, 6–14 (January/February 1984); Oi, V. T., et al., in Mishell, B. B., et al., eds., *Selected Methods In Cellular Immunology*, Chapter 17, pp. 351–372; and Kennett, R. H., et al., *Monoclonal Antibodies*, Plenum Press, N.Y., 1980, Appendix, Goding, in *Monoclonal Antibodies: Principles and Practices*, Academic Press, N.Y., 1983, pp. 118–124, which are incorporated herein by reference. Also, ascites fluids may be produced from positive clones to generate large amounts of monoclonal antibodies.

Also, a VIP receptor fragment may be conjugated to a carrier such as keyhole limpet hemocyanin, edestin, thyroglobulin or albumins, if it is not sufficiently large to be adequately immunogenic, as is understood in the art. The method of preparation of and administration of the antigenic VIP receptor varies with its nature and abundance in the particular cells employed, and general approaches depending on these particulars are well within the skill of those practicing this art. Any effective mode of preparation and administration is acceptable.

The VIP receptor preparation in suitable form is then administered to an experimental animal for generation of the antibody-producing cells. To obtain the desired polyclonal antibodies, the antisera may be harvested and the antibodies purified by standard techniques and used directly. If monoclonal antibodies directed to specific VIP receptor epitopes are desired, the procedures described above can be employed.

The desired anti-receptor antibodies can be conveniently purified using affinity chromatography, taking advantage of the ability of the desired antibodies to link tightly to the VIP receptor moiety. Anti-receptor antibodies may also advantageously be purified by cytological purification, that is, by contacting the impure receptor preparation with SCLC or NSCLC cells, washing the cells free of unbound impurities, then eluting the purified anti-receptor antibodies from the cell surface.

It is desired that the anti-VIP receptor monoclonal or polyclonal antibody be administered to mammalian subjects in substantially pure form. As used herein, the expression "substantially pure" means that, within serologically detectable limits, only one specie of antibody combining site capable of binding the VIP receptor is present. Thus, while a substantially pure antibody molecule preparation may contain more than one species of antibody combining site, such a preparation displays a single binding affinity for a VIP receptor antigen epitope. An antibody molecule in substantially pure form is typically designated a "monoclonal antibody" by those skilled in the art because such molecules are usually produced using monoclonal hybridoma cultures.

Methods for preparing paratope-containing portions of anti-VIP receptor immunoglobulin molecules such as Fab, Fab', F(ab')$_2$ and F(v) from substantially intact antibodies are well known. See, for example, U.S. Pat. No. 4,342,566, Inbar et al., *PNAS (USA)*, 69:2659 (1972), and Goding, 1983, ibid.

An anti-VIP antibody molecule of the present invention is an antibody molecule that immunoreacts with an VIP epitope and thereby neutralizes the molecule, that is to say, the immunoconjugate is incapable of acting as VIP molecule biologically.

The term "cellular receptor" as used herein for VIP refers to a protein or glycoprotein macromolecule contained within the plasma membrane of one or more types of cells in the host organism, including abnormal cells such SCLC and NSCLC cells, and which receptor macromolecule, when bound to a ligand (herein, VIP), initiates the chain of responses and events that lead to what is referred to as the physiological effect of the ligand (herein, the biological response modifier action(s) of VIP).

The examples that follow are designed merely to exemplify various embodiments of this invention and are not intended to in any way limit the scope of the invention which is set forth in the specification and appended claims.

EXAMPLE 1

Interaction of Thymosin α1 with VIP Receptors on Lung Cancer Cells

Lung cancer cells (EPLC-65H squamous cell carcinoma) were cultured in serum supplemented growth medium (RPMI 1640 containing 10% fetal bovine serum). Plasma membranes were isolated (Lee, M., et al., 1990, above) and the binding potency of THNα1 determined.

The ability of unlabeled VIP (●) and THNα1 (○) to inhibit specific binding of $^{125}$I-labeled VIP to plasma membranes was determined in 3 experiments. The means and ranges of specific binding values as a function of unlabeled peptide concentration are plotted in FIG. 1.

The data show that the specific binding of a tracer concentration of labeled VIP was inhibited in a concentration-dependent manner by unlabeled VIP and THNα1. Little specific binding of $^{125}$I-VIP to VIP receptors was inhibited by 1 nM VIP, whereas almost all specific binding was inhibited by 1000 nM VIP. The $IC_{50}$ (concentration causing 50% inhibition) for VIP was about 10 nM.

In contrast, the $IC_{50}$ for THNα1 was about 200 nM, indicating that the affinity of the VIP receptor for THNα1 is about one-twentieth that for VIP itself.

EXAMPLE 2

Inhibition by THNα1 of Cross-Linking of Labeled VIP to its Receptors of Lung Cancer Cells Plasma membranes derived from squamous cell carcinoma cell line EPLC-65H were incubated with a tracer concentration (2 nM) of $^{125}$I-labeled VIP in the absence (control) and presence of THNα1. Membranes were then washed with ice cold buffer to remove unbound labeled VIP and the bound labeled VIP covalently cross linked to its membrane receptor protein using 2 mM disuccinimidylsuberate. Membranes were solubilized with 10% SDS in electrophoresis buffer, and the protein mixture separated by SDS-PAGE electrophoresis. Gels were then radioautographed to produce X-ray films showing radioactive proteins.

Figure 2:
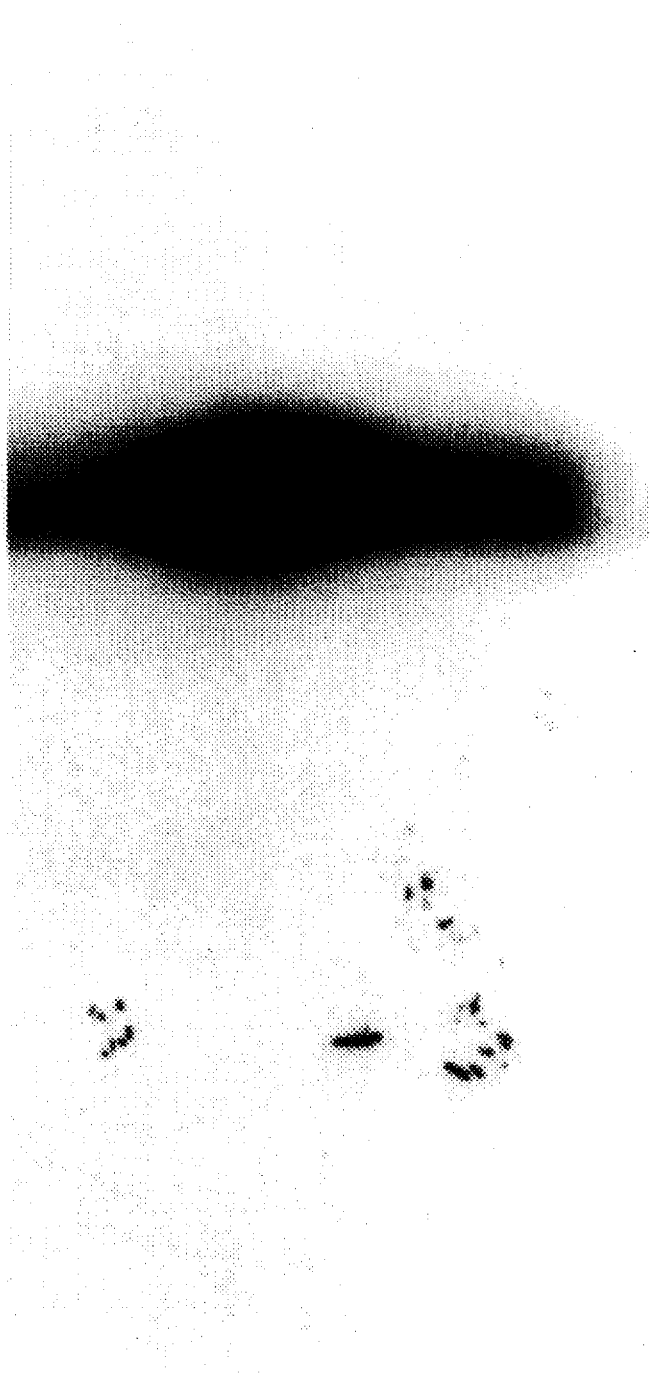
FIG. 2 is an autoradiogram showing $^{125}$I-labeled VIP cross-linked to its 82 kDa receptor protein from lung cancer cell plasma membranes in the absence (b) and presence (c) of 1 µM THN$\alpha$1, as well as 1 µM VIP (a).

As shown by the autoradiogram of FIG. 2, lane c, 1 μM THNα1 inhibited the binding of $^{125}$I-labeled VIP to a 83 kDa glycoprotein, to an extent similar to that accomplished by unlabeled VIP itself (lane a). This glycoprotein presumably is the VIP receptor in this cell line, and it also presumably is this glycoprotein by which thymosins and anti-VIP receptor antibodies inhibit the lung cancer growth promoting effects of VIP.

EXAMPLE 3

Colonization of Lung Cancer Cells In Vitro

The effects of THNα1 on the growth of lung cancer cell lines was studied. Single viable cells were plated in soft agar as previously described (Mahmoud, S., et al., *Life Sci.*, 44:367 (1989)), and, after two weeks, the colonies were stained with 0.1% p-iodonitrotetrazolium violet.

The pattern of colony staining shown in FIG. 3A demonstrates that numerous large colonies of NCI-H838 cells had formed by two weeks, whereas in the presence of 10 μM THNα1 the number and size of the colonies were dramatically reduced.

The number of colonies larger than 50 μm in diameter were counted. The data of Table I shows that 89 colonies of NCI-H157 (squamous cell carcinoma) formed. The number of colonies did not change when either 1 nM or 10 nM VIP was added, although there was a slight increase at 100 nM or 1000 nM VIP. In contrast, 10 nM THNα1 produced no change in colony number, 100 nM or 1,000 nM THNα1 produced a slight decrease, but 10,000 nM THNα1 significantly decreased colony formation.

TABLE I

Dose Response Curve of VIP and THNα1 on NCI-H157 (Squamous Cell Carcinoma) Growth

| Peptide | Colony Number | N/No |
|---|---|---|
| None | 89 ± 10 | 1.00 |
| 1 nM VIP | 89 ± 7 | 1.00 |
| 10 nM VIP | 89 ± 7 | 1.00 |
| 100 nM VIP | 113 ± 6 | 1.27 |
| 1000 nM VIP | 123 ± 16 | 1.38 |
| 10 nM THNα1 | 89 ± 8 | 1.00 |
| 100 nM THNα1 | 82 ± 3 | 0.92 |
| 1000 nM THNα1 | 74 ± 10 | 0.83 |
| 10000 nM THNα1 | 61 ± 7 | 0.69 |

The mean ± S.D. of 3 determinations is indicated. Also, the colony fraction (N/No) is calculated where No and N are the number of colonies in the absence or presence of additions respectively.

EXAMPLE 4

Effect of THNα1 and THN β4 on Growth of Lung Cancer Cell Lines

The experimental conditions of Example 3 were repeated with NCI-H720 (lung carcinoid cancer cells) and NCI-N417 (SCLC lung cancer cells) cell lines. Colonies were counted as before. The absolute and relative number of colonies of greater than 50 μm diameter are shown in Table II.

VIP at 100 nM increased colony formation for both SCLC and lung carcinoid cell lines. THNβ4 at 1 μM did not influence colony number significantly. In dramatic contrast, THNα1 at 1 μM greatly reduced colony formation for both types of lung cancer cells.

TABLE II

Specificity of Peptides on Lung Cancer Growth

| Agent | NCI-H720 (carcinoid) | N/No | N417 | (SCLC) N/No |
|---|---|---|---|---|
| control | 73 ± 24 | 1.00 | 201 ± 16 | 1.00 |
| VIP 100 nM | 100 ± 26 | 1.37 | 216 ± 40 | 1.08 |
| THNα1 1 μM | 28 ± 14 | 0.39 | 99 ± 16 | 0.49 |
| THN β4 1 μM | 68 ± 20 | 0.93 | 240 ± 68 | 1.20 |

The mean value ± S.E. of 3 determinations is indicated.

EXAMPLE 5

Effects of Thymosins on Lung Cancer in Animals

Squamous cell carcinoma (NCI-H157, $10^7$ cells) was injected subcutaneously into female Balb/c nude mice. Xenografts formed after about one week, and tumor size ($mm^3$) was followed weekly.

Figure 4:
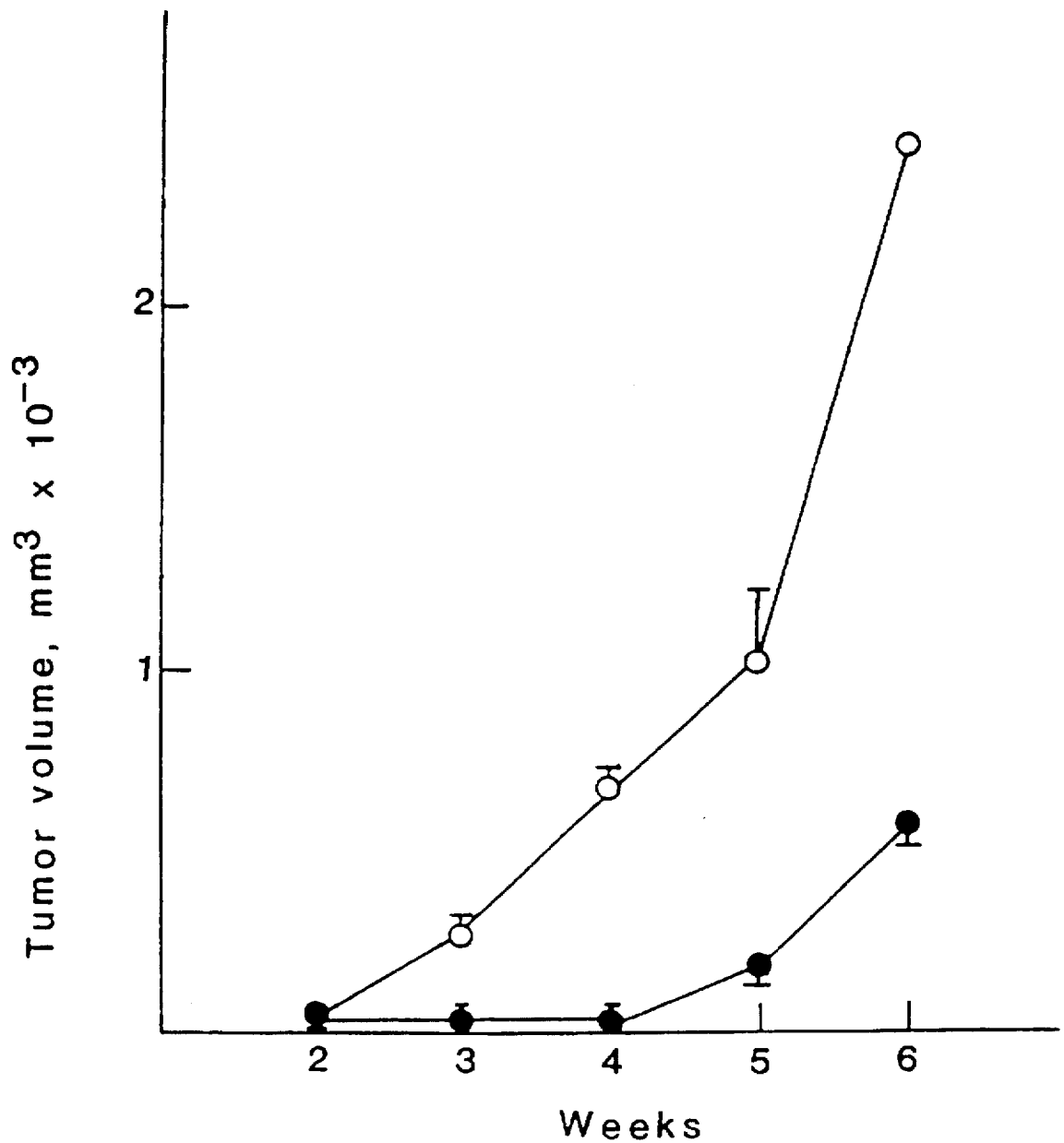
FIG. 4 shows the size of lung cancer cell xenografts in mice in the absence (○) and presence (●) of THN$\alpha$1.

THNα1, 10 μg, in a sterile pharmaceutical vehicle, was injected subcutaneously adjacent to the tumor. No toxic effects on the animals were observed. FIG. 4 shows that after two weeks a palpable mass (28 $mm^3$) was observed in control mice which received only placebo injections. Tumor growth increased exponentially over the next several weeks, and at week 6, control mice that had very large tumors (2430 $mm^3$) were killed. In dramatic contrast, mice receiving THNα1 developed a palpable mass (3 $mm^3$) only at week 3, and the tumor growth slowly increased until week 5 (187 $mm^3$). At this point, withdrawal of THNα1 resulted in the resumption of rapid tumor growth (at week 6 the tumor volume was 585 $mm^3$, still only 25% of the size of the control xenografts).

This experiment shows that THNα1 may function as a reversible inhibitor of NSCLC growth.

EXAMPLE 6

The experiment of Example 5 was repeated, except that xenografts were produced with NCI-H292 squamous cell lung carcinoma and fragments of THNα1 were compared for efficacy with the parent polypeptide.

The data of Table III show that the squamous cell carcinoma xenografts produced by NCI-H292 cells grew more slowly than did xenografts produced by NCI-H157 squamous cell carcinoma cells. After three weeks, measurable tumors (2–5 $mm^3$) were observed. By week 8, the control tumor volume had increased about 60-fold to 305 $mm^3$. THNα1 and the C- and N-terminal fragments thereof reduced tumor growth by approximately 50%. The C-terminal fragment was composed of amino acids 15 to 28 of THNα1, and the N-terminal fragment composed of amino acids 1 to 14 of THNα1.

TABLE III

Xenograft Formation of Cell Line NCI-H292

| Addition at week | 3 | 4 | 5 | 6 | 7 | 8 |
|---|---|---|---|---|---|---|
| C-fragment | 4 | 15 | 36 | 65 | 123 | 141 |
| Control | 5 | 31 | 48 | 150 | 237 | 305 |
| THNα1 | 2 | 23 | 40 | 72 | 128 | 135 |
| N-fragment | 3 | 27 | 45 | 72 | 85 | 162 |

NCI-H292 was injected into nude mice and the tumor volume (mm3) was indicated. Peptides (10 μg) were injected daily subcutaneously. The mean value of 3 determinations is indicated. Routinely the S.E. was 15% of the mean value.

EXAMPLE 7

SEQUENCE ID NO. (3)

Ac-Ser-Asp-Ala-Ala-Val-Asp-Thr-Ser-Ser-Glu-Ile-Thr-Thr-Lys-Asp- Leu-$NH_2$

Thymosin $\alpha_1$-$N_{16}$ (1–16) amide

4-Methylbenzhydrylamine Resin (2.01 g; 0.55 mmol/g) was placed in a peptide synthesis flask and washed with 40 mL of dichloromethane 3 times. The resin was then neutralized with 40 mL of 10% triethylamine for 1 minute and again for 10 minutes, then washed 3 times with dichloromethane. The neutralized resin showed a strong positive reaction to the ninhydrin test. It was then coupled with 3.0 mmol of t-Butyloxycarbonyl-L-Leucine (Boc-Leu, 0.784 g) in the presence of 3.0 mmol of N,N'-dicyclohexylcarbodiimide (DCC, 0.618 g) in dichloromethane for 150 minutes. The synthesis was continued by performing the solid phase synthesis procedure as indicated below. [Steps 1 to 11 represent all the manipulations required of a synthetic cycle wherein one amino acid residue is incorporated into the growing peptide chain attached to the resin]:

1) prewash with 50% trifluoroacetic acid in dichlormethane,
2) stir in 50% trifluoroacetic acid for 30 minutes,
3) wash 3 times with dichloromethane,
4) prewash with 10% triethylamine in dichloromethane,
5) stir in 10% triethylamine for 3 minutes,
6) wash 3 times with dichloromethane,
7) test resin for ninhydrin reaction (should be strongly positive), 8) stir the resin with 0.970 g of Boc-Asp(OBzl) (3.0 mmol) and 0.618 g of DCC (3.0 mmol) in dichloromethane for 120 minutes, 9) wash 2 times with 50% isopropanol in dichloromethane, 10) wash 3 times with dichloromethane, 11) test for ninhydrin reaction. If negative, go to next synthetic cycle. If positive, repeat steps 8 to 11.

The solid phase peptide synthesis cycle was repeated with the following amino acid derivatives, in step 8 of each cycle, sequentially, one at a time in that order, until the desired amino acid sequence was constructed: Boc-Lys(ClZ), (1.244 g); Boc-Thr(Bzl), (0.928 g); Boc-Thr(Bzl), (0.928 g); Boc-Ile, (0.720 g); Boc-Glu (OBzl), (1.01 g); Boc-Ser (Bzl), (0.886 g); Boc-Ser(Bzl) (0.886 g); Boc-Thr(Bzl), (0.928 g); Boc-Asp(OBzl), (0.970 g); Boc-Val, (0.652 g); Boc-Ala, (0.568 g), Boc-Ala, (0.568 g); Boc-Asp(OBzl), (0.970 g); Boc-Ser(Bzl), (0.886 g), and Acetic Acid (0.180 g). The resultant protected acetyl-hexadecapeptide resin, Ac-Ser(Bzl)-Asp(OBzl)-Ala-Ala-Val-Asp(OBzl)-Thr(Bzl)-Ser(Bzl)-Ser(Bzl)-Glu(OBzl)-Ile-Thr(Bzl)-Thr(Bzl)-Lys(ClZ)-Asp(OBzl)-Leu-MBHA-Resin, thus obtained weighed 4.25 g.

Part of this protected hexadecapeptide resin (1.08 g) was mixed with 2 mL of anisole and stirred with 10 mL liquid HF for 45 minutes at 0°. The excess acid was removed by evaporation at 0° in vacuo, and the residue washed with ether. The peptide material was extracted into 50 mL of 2% ammonium acetate and desalted on a Sephadex G-10 column (0.1 M acetic acid). Lyophilization of the peptide peak provided 0.204 g of crude peptide amide.

A portion of the crude peptide (100 mg) was purified on a Hamilton PRP-1 column (2.15×25 cm, 10 µ) with a buffered solvent of 53.5 g/L isopropanol in water, and eluted with 0.035M potassium phosphate, pH 5 (flow rate=5 mL/minute; monitored at 227 nm). The fractions containing pure peptide were pooled, desalted on a Sephadex G-10 column and lyophilized to yield 26 mg thymosin $\alpha_1$-$N_{16}$ amide. The material was found to be homogeneous on high performance capillary electrophoresis. Amino Acid Analysis: Asp, 3.00 (3); Thr, 2.68 (3); Ser, 2.67 (3); Glu, 1.04 (1); Ala, 1.88 (2); Val, 0.97 (1); Ile, 1.01 (1); Leu, 1.02 (1); Lys, 1.00 (1). Mass spectrometric analysis showed that the compound had the expected molecular weight; $MH^+$=1,693.8, $MNa^+$=1,716.9 (Calculated MW=1,693.8).

EXAMPLE 8

Effect of THN$\alpha_1$ and Analogs on NCI-H727 Cancer Cell Growth in vitro

The effects of thymosin $\alpha_1$, thymosin $\alpha_1$ amide and thymosin $\alpha_1$-$N_{16}$(1–16) amide were tested on growth of lung cancer cell line NCI-H727 in a procedure substantially as described in Moody et al., *Cancer Research* 53:5214–5218 (1993). Thymosin $\alpha_1$-$N_{16}$ amide was produced as set forth in Example 7. Thymosin $\alpha_1$ amide was produced as described in U.S. Ser. No. 08/246,572 filed May 20, 1994, now allowed, a continuation of U.S. Ser. No. 08/013,087, filed Feb. 3, 1993, now abandoned. The results shown in Table IV below indicate that TNH$\alpha$lamide and THN$\alpha$1-$N_{16}$(1–16) amide strongly inhibit NCI-H727 grown in vitro and may be more potent than THN$\alpha$1.

TABLE IV

Effect of THN and analogs on NCI-H727 growth in vitro.

| Addition | Colonies |
|---|---|
| None (control) | 133 ± 12 |
| THN$\alpha$1, 1 µM | 48 ± 15** |
| THN$\alpha$1amide, 1 µM | 28 ± 17** |
| THN$\alpha$1-$N_{16}$ (1–16) amide 1 µM | 22 ± 10** |

The mean value ± S.D. of 3 determinations is indicated; **, $p < 0.01$.

EXAMPLE 9

Effect of THN$\alpha$1amide and Thymosin $\alpha_1$-$N_{16}$ (1–16) amide on NCI-H510 Cancer Cell Growth in vivo In a procedure substantially as set forth in Moody et al. (1993) supra, NCI-H510 lung cancer cells were injected into nude mice, and tumors formed after one week. The compounds listed in Table V below (produced as described above) were injected (100 microliters) subcutaneously daily. Tumors were measured at week 4. The results shown in Table V below indicate that THN$\alpha$1amide and THN$\alpha$1-$N_{16}$ (1–16)amide strongly inhibit NCI-H510 growth in vivo.

TABLE V

Effects on NCI-H510 growth in vivo.

| Addition | Tumor volume, $mm^3$ |
|---|---|
| Control (PBS) | 2258 |
| THN$\alpha$1amide, 10 µg | 229 |
| THN$\alpha$1-$N_{16}$ (1–16) amide 10 µg | 410 |

The mean value of 3 tumors is indicated and the S.E. was approximately 15% of the mean value.

EXAMPLE 10

Figure 5:
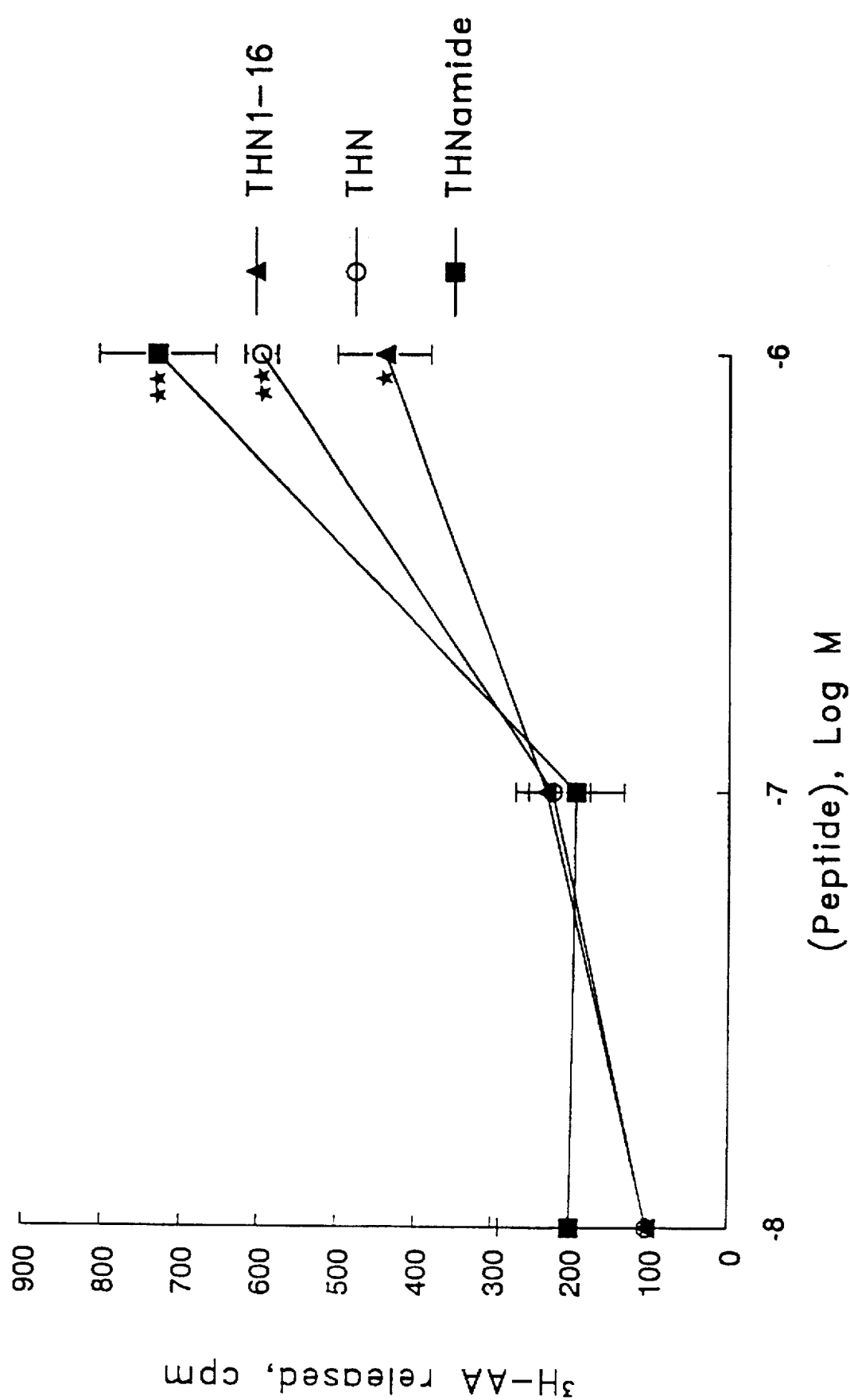
FIG. 5 shows the effects of thymosin $\alpha_1$-$N_{16}$(1–16) amide (THN1–16), thymosin $\alpha_1$ (THN) and thymosin $\alpha_1$ amide (THNamide) on $^3$H-arachidonic acid (AA) release.

Effect of Thymosin $\alpha$1-$N_{16}$(1–16)amide, Thymosin $\alpha_1$ and THN$\alpha$1amide on $^3$H-arachidonic acid (AA) Release In a procedure substantially as set forth in Moody et al. (1993) supra, NCI-H1299 lung cancer cells were loaded with $^3$H-AA overnight, and after removal of free $^3$H-AA cells, were treated with increasing concentrations of THN$\alpha$1 (1–16)amide (△), THN$\alpha$1 (○) and THN$\alpha$1amide (■) (produced as described above). The mean value ± S.E. of 4 determinations is indicated; *,$p<0.05$; ** $p<0.01$. The results shown in FIG. 5 indicate that 1 µM THN$\alpha$1, THN$\alpha$1amide and THN$\alpha$1-$N_{16}$(1–16)amide significantly stimulate $^3$H-AA release from NCI-H1299 cells in vitro.

EXAMPLE 11

Effect of THN$\alpha$1amide on NCI-H727 Tumors

Figure 6:
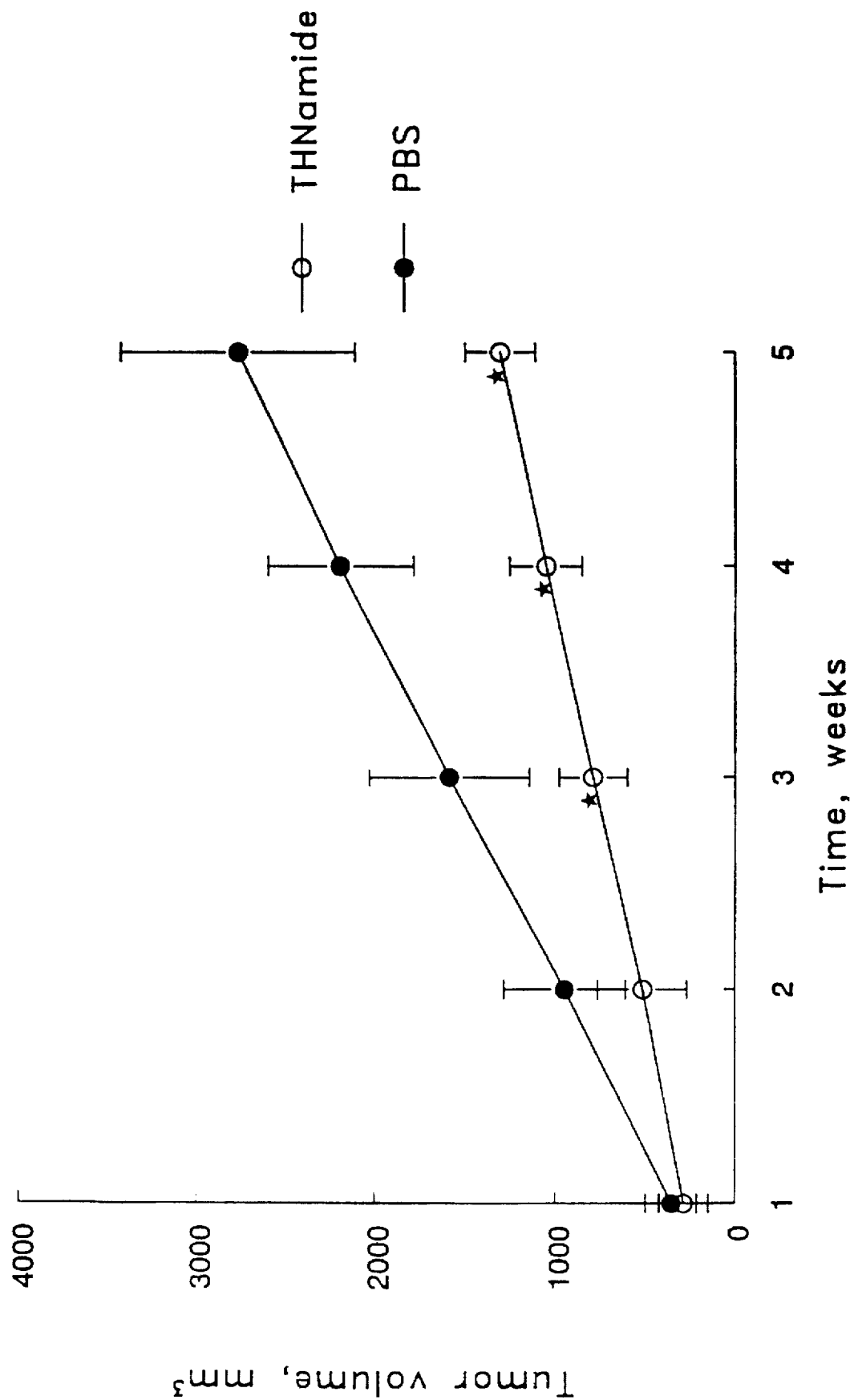
FIG. 6 shows the effect of thymosin $\alpha_1$ amide (THNamide) on lung cancer cell NCI-H727 tumors.

In a procedure substantially as set forth in Moody et al. (1993) supra, NCI-H727 cells were injected into nude mice and after 1 week xenografts formed. The mice were daily injected subcutaneously with PBS (○) as control or PBS containing 10 µg of THN$\alpha$1amide (produced as described above). The mean value ± S.E. of 3 determinations is indicated; *, $p<0.05$. The results shown in FIG. 6 indicate that THN$\alpha$1amide significantly inhibits NCI-H727 growth in vivo.

We claim:

1. A method of treating lung cancer in mammals in need of such treatment, comprising administering to said mammals an anti-cancer effective amount of a member selected from the group consisting of Thymosin α1 amide and Thymosin $\alpha_1$-$N_{16}$(1–16) amide, in a pharmaceutically acceptable vehicle.

2. The method of claim 1 wherein said lung cancer is a small cell lung cancer or a nonsmall cell lung cancer.

3. The method of claim 2 wherein said member is Thymosin α1 amide.

4. The method of claim 2 wherein said member is Thymosin $\alpha_1$-$N_{16}$(1–16) amide.

* * * * *

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
      ( A ) LENGTH: 28 Amino Acids
      ( B ) TYPE: Amino Acid
      ( D ) TOPOLOGY: Linear ( i i ) MOLECULE TYPE: Peptide ( v ) FRAGMENT TYPE: N-terminal ( i x ) FEATURE:
      ( A ) NAME/KEY: Modified-site
      ( B ) LOCATION: 1
      ( D ) OTHER INFORMATION:

( i x ) FEATURE:
      ( A ) NAME/KEY: Modified-site
      ( B ) LOCATION: 28
      ( D ) OTHER INFORMATION:

( x i ) SEQUENCE DESCRIPTION: SEQ ID NO:1:

```
His Ser Asp Ala Val Phe Thr Asp Asn Tyr Thr Arg Leu Arg Lys
1               5                   10                  15

Gln Met Ala Val Lys Lys Tyr Leu Asn Ser Ile Leu Asn
                20                  25
```

( 2 ) INFORMATION FOR SEQ ID NO:2:

( i ) SEQUENCE CHARACTERISTICS:
      ( A ) LENGTH: 28 Amino Acids
      ( B ) TYPE: Amino Acid
      ( D ) TOPOLOGY: Linear ( i i ) MOLECULE TYPE: Peptide ( v ) FRAGMENT TYPE: N-terminal ( i x ) FEATURE:
      ( A ) NAME/KEY: Modified-site
      ( B ) LOCATION: 1
      ( D ) OTHER INFORMATION:

( i x ) FEATURE:
      ( A ) NAME/KEY: Modified-site
      ( B ) LOCATION: 28
      ( D ) OTHER INFORMATION:

( x i ) SEQUENCE DESCRIPTION: SEQ ID NO:2:

```
Ser Asp Ala Ala Val Asp Thr Ser Ser Glu Ile Thr Thr Lys Asp
1               5                   10                  15

Leu Lys Glu Lys Lys Glu Val Val Glu Glu Ala Glu Asn
                20                  25
```

( 2 ) INFORMATION FOR SEQ ID NO:3:

( i ) SEQUENCE CHARACTERISTICS:
      ( A ) LENGTH: 16 Amino Acids
      ( B ) TYPE: Amino Acid
      ( D ) TOPOLOGY: Linear ( i i ) MOLECULE TYPE: Peptide ( v ) FRAGMENT TYPE: N-terminal ( i x ) FEATURE:

-continued (A) NAME/KEY: Modified-site
            (B) LOCATION: 1
            (D) OTHER INFORMATION:

(ix) FEATURE:
            (A) NAME/KEY: Modified-site
            (B) LOCATION: 16
            (D) OTHER INFORMATION:

(xi) SEQUENCE DESCRIPTION: SEQ ID NO:3:

Ser  Asp  Ala  Ala  Val  Asp  Thr  Ser  Ser  Glu  Ile  Thr  Thr  Lys  Asp
    1                   5                        10                       15

Leu